United States Patent [19]

Dunbar

[11] Patent Number: 4,830,663
[45] Date of Patent: May 16, 1989

[54] SULFONYLUREA COMPOUNDS FOR INHIBITING BOLTING IN SUGAR BEETS

[75] Inventor: Joseph E. Dunbar, Midland, Mich.

[73] Assignee: The Dow Chemical Company, Midland, Mich.

[21] Appl. No.: 11,962

[22] Filed: Feb. 6, 1987

[51] Int. Cl.⁴ .................... A01N 43/90; C07D 487/04
[52] U.S. Cl. ........................................ 71/92; 544/263
[58] Field of Search ............................ 544/263; 71/92

[56] References Cited

U.S. PATENT DOCUMENTS 4,678,502  7/1987  Hanagan ................................. 71/92

FOREIGN PATENT DOCUMENTS 2149792  6/1985  United Kingdom ................ 544/263

OTHER PUBLICATIONS

Lenton, J. R., and G. F. J. Milford, 1977, Plant Growth Regulators and the Physiological Limitations to Yield in Sugar Beet, Pestic, Sci., 8:224–229.

Longden, P. C., 1980, Control of Bolting in Sugar Beet, Joint DPGRG and BPGRG Symposium, "Aspects and Prospects of Plant Growth Regulators," Monograph 6.

Primary Examiner—Donald G. Daus
Assistant Examiner—Mark W. Noel
Attorney, Agent, or Firm—S. Preston Jones; Ronald G. Brookens

[57] ABSTRACT

The present invention is directed to novel sulfonylurea compounds, compositions and methods for controlling bolting in sugar beets.

21 Claims, No Drawings

SULFONYLUREA COMPOUNDS FOR INHIBITING BOLTING IN SUGAR BEETS

BACKGROUND OF THE INVENTION

Sugar beet flowering is controlled by a cold weather treatment of the plants known as vernalization followed by days of long, uninterrupted periods of light known as long days. As the days lengthen, the beets produce bolters which are elongated stems bearing flowers which ultimately produce seeds of indeterminate, multi-branched racemes. In Europe where large acreages of sugar beet are grown, cold spring weather following spring sowing is often enough to induce bolting of the beets. This bolting causes various problems to the farmer who grows the beet for the sugar content of the beet root. One problem is that bolting reduces both the size and the sugar content of the beet root since the products of photosynthesis are diverted to flower production. Another problem is that bolting causes processing difficulties due to lignification of the root, since the presence of lignin reduced the efficiency with which sugars can be extracted. Bolters also physically interfere with mechanical harvesting by becoming entangled in harvesting machinery. Another problem is that bolted plants cause a large amount of competition by shading adjacent plants, thereby reducing their root size. With time, the seed from early bolters produce a weed beet with an annual habit requiring little or no vernalization. This weed beet, besides causing severe competition, prevents "beet-free periods" which are necessary for the control of beet yellowing virus.

If bolting could be completely prevented, this would be a possible means of realizing the potential physiological advantages of autumn sowing. Greater utilization of the season would be achieved by the capturing of radiation which normally falls on bare ground. Yield increases of up to 25 percent have been predicted from autumn as opposed to spring sowing. Clearly, there is a need for compounds which can control and/or prevent bolting in sugar beets.

SUMMARY OF THE INVENTION

The present invention is directed to novel compounds, compositions and methods for controlling bolting in sugar beets. The method comprises applying to the sugar beets an amount effective to control bolting in sugar beets of a compound of the formula:

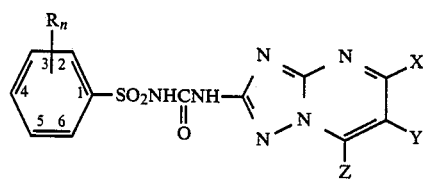

wherein
R is alkyl, halo or carboalkoxy;
n is 0, 1 or 2; and
X, Y and Z independently represent hydrogen, alkyl, halo, or $CF_3$.

Preferably, R is alkyl, more preferably methyl. Also preferred is that R is carboalkoxy, more preferably carbomethoxy. R is preferentially substituted in the 4 position for alkyl and in the 2- or the 6-position for carboalkoxy. Also preferred is that X and Z are alkyl, more preferably methyl and Y is hydrogen.

The present invention has the advantage of inhibiting bolting in sugar beets and permits earlier planting thereof with subsequently higher yields.

DETAILED DESCRIPTION OF THE INVENTION

The term "alkyl" is used in the present specification and in the appended claims to designate a straight or branched saturated hydrocarbon moiety (i.e., hydrocarbons having carbon-carbon single bonds) containing from 1 to 8 carbon atoms, such as, for example, methyl, ethyl, propyl, isopropyl, butyl, isobutyl, tertbutyl, pentyl, hexyl and the like.

The term "carboalkoxy" is meant to mean the ester moiety

wherein R is alkyl as defined hereinabove, such as carbomethoxy, carboethoxy, carbopropoxy, carbobutoxy, carbopentoxy, carboxyhexoxy and the like.

The term "halo" is intended to mean chloro, bromo, fluoro or iodo.

The sulfonylurea compounds of the present invention can be prepared by contacting an arenesulfonylisocyanate compound of Formula II with a triazolopyrimidine compound of Formula III to form the desired sulfonylurea of Formula I, as shown in the following preparative scheme:

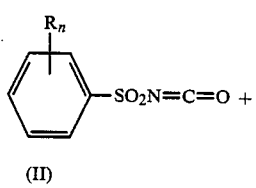

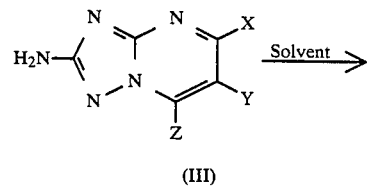

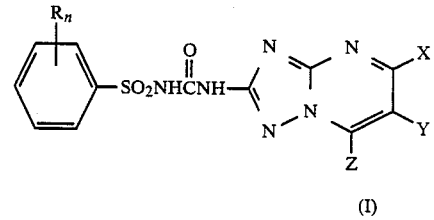

The arenesulfonyl isocyanate compounds of Formula (II) can be contacted with the triazolopyrimidine compounds of Formula (III) in molar ratios ranging from about 1:1 to about 5:1, more preferably about 1.5:1 most preferably about 1.03:1 (arenesulfonyl isocyanate:triazolopyrimidine).

The contacting of the arenesulfonyl isocyanate and triazolopyrimidinyl starting materials is normally carried out in the presence of a suitable inert organic solvent, such as toluene, methylene chloride, chloroform, benzene, xylene and the like, preferably toluene. Alternatively, the contacting of the arenesulfonyl isocyanate and the triazolopyrimidinyl starting materials can be conducted neat, i.e., in the absence of added inert organic solvent where the arene-sulfonyl isocyanate is in excess.

The contacting of the arenesulfonyl isocyanate and the triazolopyrimidinyl compounds can be carried out at temperatures ranging from about 25° to 150° C., preferably from about 80° to about 115° C. The contacting is normally carried out at ambient pressures with stirring or other means of agitation for periods of 0.5 hour or more.

After the reaction is completed, the desired sulfonylurea compound of Formula I is recovered by conventional recovery procedures such as filtration, recrystallization, washing, distillation and the like.

The following examples illustrate the present invention in a manner by which it can be practiced but, as such, should not be construed as limitations upon the overall scope of the same.

EXAMPLE 1

N-(((5,7-Dimethyl-1,2,4-triazolo(1,5a)pyrimidin-2-yl)amino)carbonyl)-4-methylbenzenesulfonamide

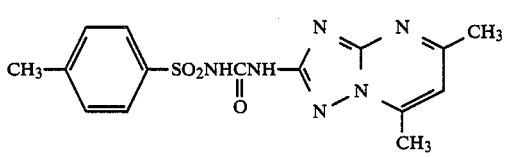

To a stirred suspension of 4.90 grams (g) of 2-amino-1,2,4-triazolo(1,5a)-5,7-dimethylpyrimidine in 130 milliliters (ml) of dry toluene is added 4.7 ml (6.1 g) of p-toluenesulfonyl isocyanate. The stirred reaction mixture is heated at reflux for one hour and then allowed to cool to room temperature. The white, crystalline solid product is collected on a filter, washed first with toluene and then with hexane and air dried; weight of 10.7 g (99% yield), melting point (mp) 225-225.5 decomposition (dec.) Nuclear Mangetic Resonance (NMR) (CF$_3$COOD), δ 11.22 (s, 2, CF$_3$CO$_2$H (NH protons)), 7.89 (d, 2, J=8 Hz, arom.), 7.44 (s, 1, het. ring proton), 7.37 (d, 2, J=8 Hz, arom.), 2.91 (s, 3, het. ring CH$_3$), 2.83 (s, 3, het. ring CH$_3$) and 2.48 parts per million (ppm) (s, 3, tolyl CH$_3$).

| Analysis: | | | | |
|---|---|---|---|---|
| | C | H | N | S |
| Calculated for C$_{15}$H$_{16}$N$_6$O$_3$S: | 49.99 | 4.48 | 23.32 | 8.9 |
| Found: | 50.2 | 4.53 | 23.34 | 9.18 |

EXAMPLE 2

N-(((5,7-Dimethyl-1,2,4-triazolo(1,5a)pyrimidin-2-yl)amino)carbonyl)-2-(carbomethoxy)benzenesulfonamide

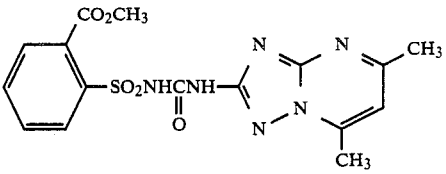

A mixture of 6.64 g of methyl 2-(isocyanatosulfonyl)-benzoate and 3.0 g of 2-amino-5,7-dimethyl-1,2,4-triazole(1,5a)pyrimidine in 100 ml of dry toluene is heated at reflux with stirring for 40 minutes. The reaction mixture is allowed to cool to room temperature and then is further cooled by means of an ice bath to give 7.08 g (95% yield) of a white, crystalline solid, mp 214.5° dec. NMR (DMSO-d$_6$, CF$_3$CO$_2$D) 14.78 (s, 2, CF$_3$CO$_2$H), 8.20 (m, 1, arom.), 7.70 (m, 3, arom.), 7.25 (s, 1, het. ring proton), 2.77 (s, 3, ring CH$_3$) and 2.68 ppm (s, 3, ring CH$_3$).

| Analysis: | | | | |
|---|---|---|---|---|
| | C | H | N | S |
| Calculated for C$_{16}$H$_{16}$N$_6$O$_5$S: | 47.52 | 3.99 | 20.78 | 7.93 |
| Found: | 47.8 | 4.1 | 20.66 | 7.7 |

EXAMPLE 3

N-(((5,7-Dimethyl-1,2,4-triazolo(1,5a)pyrimidin-2-yl)amino)carbonyl)-4-chlorobenzenesulfonamide

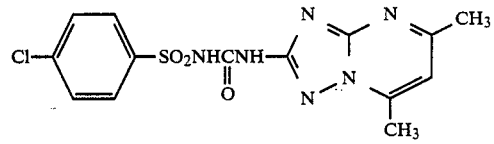

A stirred mixture of 3.4 milliliters (ml) (5.0 g) of 4-chlorobenzenesulfonyl isocyanate and 3.64 g of 2-amino-1,2,4-triazolo(1,5a)-5,7-dimethylpyrimidine in 100 ml of dry toluene is heated at reflux for three hours. The mixture is then cooled by means of an ice bath to give 7.92 g (93% yield) of a white, crystalline solid, mp 223.5° dec. The crude solid is dissolved in a solution of 100 ml of water, containing 15 ml of 20% aqueous sodium hydroxide. The solution is filtered to remove a small amount of insolubles and the filtrate acidified with concentrated hydrochloric acid to precipitate 7.0 g (82% yield) of a pure, white, crystalline solid, mp 215°-216° dec. NMR (DMSO-d$_6$, CF$_3$COOD) δ 8.04 (d, 2, J=8 Hz, arom.), 7.58 (d, 2, J=8 Hz, arom.), 7.03 (s, 1, het. ring proton), 2.67 (s, 3, CH$_3$) and 2.59 ppm (s, 3, CH$_3$).

| Analysis: | | | | |
|---|---|---|---|---|
| | C | H | N | S |
| Calculated for C$_{14}$H$_{13}$N$_6$O$_3$S: | 44.16 | 3.44 | 22.07 | 8.42 |
| Found: | 43.9 | 3.38 | 22.05 | 8.32 |

PREPARATION OF STARTING MATERIALS

The arenesulfonyl isocyanates of Formula II and the triazolpyrimidine compounds of Formula III are compounds known to those skilled in the art. Methods for preparing these starting materials can be found in U.S. Pat. Nos. 4,238,621 and J. Chem. Soc., C 1966 (22) 2031-8 whose preparative teachings are hereby incorporated by reference.

The terms "inhibiting" and "controlling" as in regards to bolting in sugar beets are regarded as equivalent terms.

The compounds of the present invention are useful as plant growth regulators for inhibiting bolting in sugar beets. The properties of these compounds in plants can be demonstrated by contacting a plant with the subject compounds, whose application may be either preemergent or postemergent, preferably postemergent.

In particular, it has been discovered that the bolting in sugar beets can be inhibited by contacting such plants and/or their habitats with compositions containing an amount effective to inhibit bolting in sugar beets of at least one of the sulfonylurea compounds disclosed herein. When the sugar beets are contacted with compositions containing one or more of the sulfonylurea compounds in dosages sufficient to supply from about 0.01 to about 10.0 pounds (lb) of the compound per acre, an acceptable inhibition of bolting in such plants can be obtained. The sulfonylurea compounds can be applied to plants during their vegetative and before their flowering stage, preferably during their vegetative stage. For example, the sulfonylurea compounds can be applied to plant parts during vegetative stages such as during their first 2-3 tree leaf stage. Preferably, the sulfonylurea compounds are applied at a rate of 0.1 to 8 lb/acre, more preferably from about 0.1 to about 1.0 lb/acre.

Not all the compounds of the present invention are equally effective in inhibiting bolting. When applied to the same plant species, some compounds are more effective at a lower dosage rate than are other compounds.

The application to plants, plant-parts, rooting zones and/or their habitats of a composition containing an amount effective to control or inhibit bolting in sugar beets of a sulfonylurea compound is essential and critical for the practice of the present invention. The exact dosage to be supplied by the composition in a given operation can depend upon the sugar beet species and upon the stage of growth and hardiness thereof as well as upon the plant part to be exposed to the composition. Other factors, such as, for example, weather, bacteria and other organisms found in the soil must also be considered.

Compositions comprising a sulfonylurea compound with an inert material known as an agricultural adjuvant or carrier in solid or liquid form allow proper application of an effective amount of the active ingredient. The sulfonylurea compounds are mixed in such quantity of ultimate treating material that adequate coverage of all plants and plant-parts or adequate admixture with their habitats (e.g., soil) can be obtained. An adjuvant is defined herein as any substance in a formulation or added to the formulation to improve activity or application characteristics to the plant parts. Good results are obtained when employing a carrier material in relatively small, but effective amounts. Generally, however, the best results are obtained by employing either a surface wetting agent, in an amount sufficient to emulsify the sulfonylurea compound or using small amounts of an organic solvent with water as a carrier, for example, in an amount which the sulfonylurea compound represents from 50-99 percent by weight, of the total treating material. Such agents provide proper intimate contact of the sulfonylurea compound with the plant.

The exact concentration of the sulfonylurea compounds employed in the compositions for application to plants, plant-parts and/or their habitats is not critical and can vary considerably provided the required dosage of effective agent is supplied to the plant, plant-part, rooting zone, and/or habitat treated. The concentration of the sulfonylurea compound in liquid compositions employed to supply the desired dosage generally is from about 0.01 to about 50 percent by weight, preferably from about 12 to about 50 percent, although concentrations as high as 96 percent by weight can be conveniently employed. In finely divided solid carrier compositions, the concentration of the sulfonylurea compound can be from 0.1 to 60 percent by weight. In compositions to be employed as concentrates, the sulfonylurea compound can be present in a concentration of from about 5 to about 98 percent by weight.

Liquid compositions employed as a spray containing the desired amount of active ingredient can be prepared by dissolving the sulfonylurea compound in a small amount of an organic liquid carrier or by dispersing the sulfonylurea compound in water with or without the aid of a suitable surface wetting agent such as an ionic or non-ionic emulsifying agent. The aqueous compositions can contain one or more water immiscible solvents for the sulfonylurea compound. In such compositions, the carrier comprises an aqueous emulsion, i.e., a mixture of water, emulsifying agent and a low concentration of a water miscible solvent. The choice of dispersing and emulsifying agent, and the amount thereof employed is dictated by the nature of the composition and by the ability of the agent to facilitate the dispersion of the sulfonylurea compound in the carrier to produce the desired composition. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps, and the like.

In the preparation of dust compositions, the active ingredient is dispersed in and on a finely divided solid carrier such as clay, talc, chalk, gypsum, bentonite, fuller's earth, attapulgite, and the like. In such operation, the finely divided carrier is mechanically mixed or ground with the sulfonylurea compound. Depending upon the proportion of ingredients, these dust compositions can be employed as concentrates and subsequently diluted with additional solid carrier or with liquid or solid surface-active dispersing agents to obtain the desired amount of active ingredient in a composition adapted to be employed for the control or inhibition of bolting in the sugar beets. Also, such dust compositions, particularly when finely ground or milled, can be dispersed in water, preferably with the aid of a surface-active dispersing agent, to form spray mixtures.

Suitable adjuvants useful in making up compositions of the foregoing type are well known to those skilled in the art. The methods of applying the solid or liquid formulations similarly are well known to the skilled artisan.

Satisfactory results are obtained when the sulfonylurea compositions are combined with other agricultural materials intended to be applied to plants, plant-parts and/or their habitats. Such materials include fertilizers, fungicides, insecticides, acaricides, nematocides, bactericides, soil conditioning agents, herbicides and the like.

When operating in accordance with the present invention, compositions containing amounts effective to control bolting in sugar beets of the sulfonylurea compounds are applied to plants, plant-parts and/or their habitats in any convenient fashion. Applications to a plant habitat, e.g., soil, can be carried out by simply mixing with the habitat, such as by applying to the surface of soil by spraying a liquid composition and thereafter dragging or discing into the soil to the desired depth or by employing a liquid carrier to accomplish the penetration and impregnation. The application of spray and dust compositions to the surface of soil can be carried out by conventional methods, e.g., power dusters, boom and hard sprayers, and spray dusters.

In a further method, the distribution of the sulfonylurea compositions in soil can be accomplished by introducing the active ingredient in the water employed to irrigate the soil. In such procedures, the amount of water can be varied with the porosity and water holding capacity of the soil to obtain a desired depth of distribution of the agent.

In addition, the present method also comprehends the employment of an aerosol composition containing a sulfonylurea compound as an active compound. Such a composition is prepared according to conventional methods wherein the active ingredient is dispersed in a solvent, and the resultant dispersion mixed with a readily volatilized liquid propellant. Such variables, as the particular active ingredient to be used and the particular plant part to be treated, will determine the identity of the solvent and the concentration of the active ingredient therein. Examples of suitable solvents are water, and low concentrations of an organic solvent such as acetone, isopropanol, and 2-ethoxyethanol. Also, employment of the sulfonylurea compound in pastes, gels, foams, invert emulsions, and the like, as well as pigmented or unpigmented pelleted solids is contemplated.

The following example further illustrates the present invention.

EXAMPLE 4

Sugar beets are grown in potting media in pots in a greenhouse. The plants are treated when they have 2–3 true leaves. Plants are sprayed to run-off with an aqueous solution containing the test chemical at a concentration of 400 parts per million (ppm) and 0.1 percent Tween 20 wetting agent. The plants are maintained in a greenhouse with supplemental lighting to a 14.5 hour photoperiod and a minimum night temperature of 65° F. (18° C.). The maximum day temperature, humidity and light intensity are all variable. Final readings are made about 2 weeks after spraying. Readings represent the change in the property measured as a percentage of an untreated control. Thus, results of 100 percent indicate complete inhibition or control of bolting compound with the untreated control. Results less than 100 percent indicate less than complete bolting inhibition compared with the untreated controls. The results are provided in Table 1.

TABLE 1

| Control of Bolting in Sugarbeets | |
|---|---|
| Compound | Percent Control of Bolting |
| N—(((5,7-Dimethyl-1,2,4-triazolo(1,5a)pyrimidin-2-yl)amino)carbonyl)-4-methylbenzenesulfonamide | 100 |
| N—(((5,7-Dimethyl-1,2,4-triazolo(1,5a)pyrimidin-2-yl)amino)carbonyl)-2-(carbomethoxy)-benzenesulfonamide | 90 |

What is claimed is:

1. A compound of the formula:

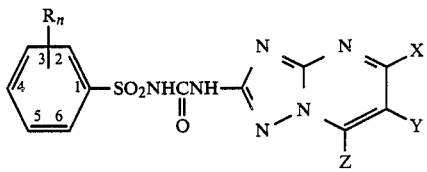

wherein
R is alkyl or carboalkoxy;
n is 0, 1 or 2; and
X, Y and Z independently represent hydrogen, alkyl, halo, hydrogen or $CF_3$.

2. The compound of claim 1 wherein R is alkyl.

3. The compound of claim 2 wherein R is methyl substituted in the 4-position on the phenyl ring.

4. The compound of claim 1 wherein R is carboalkoxy.

5. The compound of claim 4 wherein R is carbomethoxy substituted in the 2-position on the phenyl ring.

6. The compound of claim 1 wherein X and Z are alkyl and Y is hydrogen.

7. The compound of claim 4 wherein X and Z are methyl and Y is hydrogen.

8. The compound of claim 1 wherein R is methyl substituted in the 4-position, X and Z re methyl and Y is hydrogen.

9. The compound of claim 1 wherein R is carbomethoxy substituted in the 2-position in the phenyl ring, X and Z are methyl and Y is hydrogen.

10. A composition comprising an inert agricultural carrier and amount effective to control bolting in sugar beets of a compound of the formula:

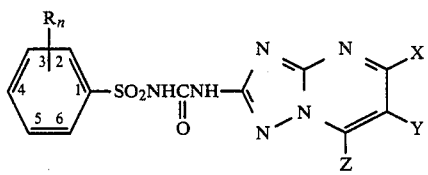

wherein
R is alkyl or carboalkoxy;
n is 0, 1 or 2; and
X, Y and Z independently represent hydrogen, alkyl, halo or $CF_3$.

11. The composition of claim 10 wherein R is alkyl.

12. The composition of claim 10 wherein R is methyl substituted in the 4-position on the phenyl ring.

13. The composition of claim 10 wherein R is carboalkoxy.

14. The composition of claim 10 wherein R is carbomethoxy substituted in the 2-position on the phenyl ring.

15. The composition of claim 10 wherein X and Z are alkyl and Y is hydrogen.

16. The composition of claim 15 wherein X and Z are methyl and Y is hydrogen.

17. The composition of claim 16 wherein R is methyl substituted in the 4-position on the phenyl ring, X and Z are methyl and Y is hydrogen.

18. The composition of claim 10 wherein R is carbomethoxy substituted in the 2-position on the phenyl ring, X and Z are methyl and Y is hydrogen.

19. A method for inhibiting the bolting of sugar beets which comprises applying to the locus of said sugar beets a bolting inhibiting amount of a compound of the formula

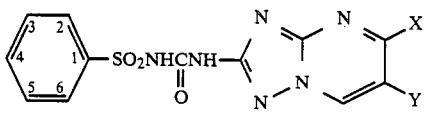

wherein
R is alkyl or carboalkoxy;
N is 0, 1 or 2; and
X, Y and Z independently represent hydrogen, alkyl, halo or $CF_3$.

20. The method of claim 19 wherein R is methyl substituted in the 4-position, X and Z are methyl and Y is hydrogen.

21. The method of claim 19 wherein R is carbomethoxy substituted in the 2-position on the phenyl ring, X and Z are methyl and Y is hydrogen.

* * * * *